United States Patent [19]
Hale et al.

[11] Patent Number: 6,120,766
[45] Date of Patent: Sep. 19, 2000

[54] CDW52-SPECIFIC ANTIBODY FOR TREATMENT OF MULTIPLE SCLEROSIS

[76] Inventors: Geoffrey Hale; Herman Waldmann, both of University of Cambridge, Department of Pathology, Immunology Div., Tennis Court Road, Cambridge, CB2 1QP, United Kingdom

[21] Appl. No.: 08/244,316

[22] PCT Filed: Dec. 4, 1992

[86] PCT No.: PCT/GB92/02252

§ 371 Date: Jun. 22, 1994

§ 102(e) Date: Jun. 22, 1994

[87] PCT Pub. No.: WO93/10817

PCT Pub. Date: Jun. 10, 1993

[30] Foreign Application Priority Data

Dec. 4, 1991 [GB] United Kingdom .................... 9125768

[51] Int. Cl.[7] .................................................. A61K 39/395
[52] U.S. Cl. ..................... 424/130.1; 424/133.1; 424/137.1; 424/154.1; 435/69.6; 530/387.3; 530/387.5; 530/388.2; 530/388.73; 530/388.75; 530/395; 536/23.53
[58] Field of Search .............................. 424/130.1, 154.1, 424/133.1, 137.1; 435/69.6, 240.27; 530/388.2, 387.3, 387.5, 388.73, 388.75, 395; 536/23.53

[56] References Cited

U.S. PATENT DOCUMENTS

| | | | |
|---|---|---|---|
| 5,545,403 | 8/1996 | Page ...................................... | 424/133.1 |
| 5,545,404 | 8/1996 | Page et al. ........................... | 424/133.1 |
| 5,545,405 | 8/1996 | Page ...................................... | 424/133.1 |

FOREIGN PATENT DOCUMENTS

| | | | |
|---|---|---|---|
| 0328404 | 8/1989 | European Pat. Off. . | |
| 328404 | 8/1989 | European Pat. Off. ..... | A61K 39/395 |

OTHER PUBLICATIONS

Riechmann et al, "Reshaping human antibodies for therapy", Nature 322:323–327 (1988).

Page et al, "High Level Expression of the Humanized Monoclonal Antibody Campath–1H in Chinese Hamster Ovary Cells", Bio/Technology 9:64–68 (1991).

Myers, L.W. et al, Clinical Neuropharmacology, 8(1):119–141, Feb. 1990.

Beer, S. et al, Schweiz. Med. Wschr, 121:961–969, 1991.

Weber et al, J of Neuro. vol. 22:1–9 (1989).

*Primary Examiner*—Christopher L. Chin
*Attorney, Agent, or Firm*—Kubovcik & Kubovcik

[57] ABSTRACT

The invention relates to the use of an antibody recognizing the Cdw52 antigen in the treatment of multiple sclerosis. Preferably, the antibody is the humanized antibody in the humanized antibody CAMPATH-1H.

6 Claims, No Drawings

CDW52-SPECIFIC ANTIBODY FOR TREATMENT OF MULTIPLE SCLEROSIS

The present invention relates to a method of treatment of certain auto-immune conditions in a human or animal subject.

The cells and molecules in an animal body do not normally stimulate an adaptive immune response in that body as a result of a number of mechanisms which ensure a state referred to as "self-tolerance". However, in certain circumstances these mechanisms may fail to prevent the stimulation of such an immune response and this condition is referred to as "auto-immunity". A number of diseases in humans and animals are now thought to result from auto-immunity.

Multiple sclerosis is a demyelinating disease of the central nervous system the onset of which generally occurs within the age range from about 15 to 45. Myelin is a fatty substance which forms a sheath around certain nerve fibres and which conducts nervous impulses at a rate which enables muscles to make precise and delicate movements. The disease is characterised by induration of the sheath substance leading to the formation of plaques of varying size and location which interfere with the impulses normally conducted by the sheath. The course of the disease can be highly variable in individual patients and may be subject to periods of spontaneous remission. However, the disease generally results in progressive deterioration of the control of muscle function with ultimate paralysis in many cases. The precise cause of multiple sclerosis is unknown and it may result form a complex interaction of a number of different factors. However, it is now generally recognised that there is at least an autoimmune component in the causation of the disease.

The CDw52 antigen (a 23 kDa glycoprotein also referred to as CAMPATH-1) is strongly expressed on the surface of all human lymphocytes and most monocytes but is absent from other blood cells including stem cells. A number of antibodies have been developed directed against CDw52 which is an unusually good target for complement-mediated attack. Antibodies against CDw52 bind to all lymphocytes and monocytes but lyse only lymphocytes (T and B) in vivo. Antigens similar to CDw52 are expressed in other mammalian species.

Antibodies which have been developed against CDw52 and which have been used in therapy include the following:

CAMPATH-1M is a rat IgM monoclonal antibody which has been used extensively in vitro for purging bone marrow harvests in order to deplete the T cell population prior to bone marrow transplanation. Marked reduction in the incidence and severity of graft-versus-host disease has been seen with this therapy.

CAMPATH-1G is a rat IgG2b class-switch variant of an IgG2a antibody recognising the CDw52 antigen which has been used in vivo to achieve immunosupression in more than 100 patients undergoing organ and bone marrow transplantation, management of organ rejection and treatment of haematologic malignancies with a high level of success. However, the rapid development of an anti-rat immunoglobulin response, including the possibility of anaphylaxis, is likely to limit the use of rat monoclonal antibodies against the CDw52 antigen in humans in vivo.

CAMPATH-1H is a genetically manipulated IgG antibody obtained by grafting the complementarity determining regions from CAMPATH-1G into human framework regions. The resulting "humanized" antibody is highly effective in vitro being equivalent to the rat monoclonal antibody at complement lysis and two to four times better in cell-mediated lysis of human lymphocytes. No limiting antiglobulin response is anticipated with this humanized antibody.

Expression of CAMPATH-1H was achieved initially in rat myeloma cells by placing DNA encoding the engineered antibody chains in genomic context under control of the immunoglobulin promoter/enhancer. CAMPATH-1H has recently been expressed to high levels in Chinese hamster ovary (CHO) cells.

It has now surprisingly been found that antibodies against the CDw52 antigen may be effective in the treatment of multiple sclerosis.

The present invention provides a method of treatment of a human subject suffering from multiple sclerosis which comprises administering to the said subject an effective amount of an antibody recognising the CDw52 antigen.

The present invention also provides the use of an antibody recognising the CDw52 antigen for the manufacture of a medicament for the treatment of multiple sclerosis.

It is preferred to use an anti-CDw52 antibody which does not carry with it the risk of the development of an immune reaction against the antibody itself. Accordingly whilst it is possible to use mouse or rat monoclonal antibodies it is preferred to use antibodies which have been produced by recombinant DNA technology and which have been engineered to reduce the risk of causing an immune reaction. Thus it is possible to use a chimeric antibody in which the constant domains of a mouse or rat anti-CDw52 antibody have been replaced by the constant domains of a human antibody. However, it is preferred to use a humanized or CDR-grafted antibody for the treatment of humans, i.e. an antibody in which the complementarity determining regions from a mouse or rat antibody are combined with framework regions and constant domains form one or more human antibodies.

Most preferably the method according to the invention is carried out using the CDR-grafted antibody CAMPATH-1H (see Riechmann et al, *Nature,* 322, 323–327 (1988)). As noted above, the antibody CAMPATH-1H can be produced in rat myeloma cells as originally described or it can be produced in any other expression system, particularly an expression system suitable for the production of a correctly folded, glycosylated, mammalain protein. High yields of CAMPATH-1H have been obtained by expression in a genetically manipulated CHO cell line (Page and Sydenham, *Biotechnology,* 9, 64–68 (1991)).

The dosage of anti-CDw52 antibody, preferably CAMPATH-1H, to be administered to a patient suffering from multiple sclerosis will vary with the precise nature of the condition being treated and the recipient of the treatment. The dose will generally be in the range 1 to about 100 mg for an adult patient, usually administered daily for a period between 1 and 30 days. The preferred daily dose is 1 to 10 mg per day although in some instances larger doses of up to 40 mg per day may be used.

The anti-CDw52 antibody, particularly CAMPATH-1H will generally be administered to the patient in the form of a pharmaceutical formulation. Such formulations preferably include, in addition to the antibody, a physiologically acceptable carrier or diluent, possibly in admixture with one or more other agents such as other antibodies or drugs, such as an antibiotic. Suitable carriers include, but are not limited to, physiological saline, phosphate buffered saline, phosphate buffered saline glucose and buffered saline. Alternatively the antibody may be lyophilized (freeze dried) and reconstituted for use when needed by the addition of an aqueous buffered solution as described above. Routes of administration are routinely parenteral, including intravenous, intramuscular, subcutaneous and intraperitoneal injection or delivery.

The anti-CDw52 antibody may be administered in combination with or sequentially with other drugs, in particular other drugs conventionally used in the treatment of multiple sclerosis, such as steroids, for example hydrocortisones such as methyl prednisolone, or other medicaments for the alleviation of specific symptoms of the disease. Sequential administration of the antibody with another drug may be appropriate in some cases.

The invention is illustrated by the following case history of a patient treated with the CDR-grafted anti-CDw52 antibody CAMPATH-1H. The antibody used was produced by expression in a recombinant CHO cell line (Page and Sydenham, *Biotechnology*, 9, 64–68 (1991)) followed by extraction from the cell culture medium and purification.

It is to be understood that the following case history is not intended to be in any way limiting on the scope of the invention.

CASE HISTORY

The patient was a 43 year old female who sought medical attention after 10 days of progressive loss of sensation in her perineum. She had also experienced several episodes of urinary and fecal incontinence. Clinical evaluations were remarkable for normal visual evoked responses, multiple white matter abnormalities in the cerebral hemispheres identified by brain MRI, and oligoclonal bands in the CSF; a diagnosis of multiple sclerosis was made.

Treatment with high-dose iv methylprednisolone induced an incomplete recovery (decreased incontinence with continued perineal numbness and stiff legs). Four months after initially seeking medical attention, the patient had an episode of left-sided facial pain and left leg numbness consistent with brainstem demyelinating. Over the next twelve months symptoms gradually worsened and at the end of this period the patient was admitted to hospital with left optic neuritis and Lhermitte's phenomenon. A second course of iv methylprednisolone (500 mg/day for five days) was associated with limited improvement. The disease was judged to have entered a chronic progressive phase and over the next few months the patient suffered further identifiable episodes of brainstem demyelination and left optic neuritis.

Twenty months after she initially sought medical attention, the patient received treatment with CAMPATH-1H (2 mg/day iv for five days, two days rest, then 10 mg/day iv for five days). Lymphocyte depletion was rapid, falling to $0.2 \times 10^6$ cells/L on the second dosing day from a pretreatment value of $3.8 \times 10^9$ cells/L. Lymphocyte counts remained less than $0.3 \times 10^9$ for approximately one month and then rose slowly to a value of $1.07 \times 10^9$ cells/L three months after treatment. CRP, within normal limits prior to treatment, increased to 140 mg/L, fell, and increased again to 91 mg/L on dosing days three and nine, respectively. This "double-peaked" pattern was also seen with neutrophils which increased during the same time course and coincided with the second and third dosing days at 2 and 10 mg respectively (10 mg doses followed a two day rest).

Disease activity was not significantly altered during or immediately following CAMPATH-1H treatment. Kurtzke neurological status at approximately one and two months after initiation of treatment was improved to a composite score of 11 from a pretreatment score of 14. A second rating system for scoring disease activity in demyelinating disease also documented improvement in the progression, disability and relapse assessment categories.

The 10 dose CAMPATH-1H treatment course was well tolerated. Fever and headache were reported as adverse events with both occurring with administration of the first 2 mg and 10 mg doses. Also reported was transient left-sided visual disturbance on day three, the significance of which was unclear in the light of the pre-existing left optic neuritis.

Approximately 18 months after the treatment with CAMPATH-1H, the improvement in the condition of the patient had been maintained.

What is claimed is:

1. A method for the treatment of a human subject suffering from multiple sclerosis which comprises administering to said subject an effective amount of a humanized antibody CAMPATH-1H and an effective amount of a steroid.

2. A method in accordance with claim 1, wherein the antibody is administered daily at a dose ranging from 1 to 100 mg per day for a period of 1 to 30 days.

3. A method in accordance with claim 2, wherein the antibody is administered daily at a dose ranging from 1 to 10 mg per day.

4. A method in accordance with claim 1, wherein the steroid is a hydrocortisone.

5. A method in accordance with claim 1, wherein the antibody was produced in Chinese Hamster Ovary (CHO) cells.

6. The method according to claim 4 wherein the hydrocortisone is methylprednisone.

* * * * *